United States Patent [19]

Gelbein et al.

[11] 4,116,967

[45] Sep. 26, 1978

[54] PRODUCTION OF CARBOXYLIC ACIDS FROM NITRILES

[75] Inventors: Abraham P. Gelbein, Plainfield; Morgan C. Sze, Upper Montclair, both of N.J.

[73] Assignee: The Lummus Company, Bloomfield, N.J.

[21] Appl. No.: 730,385

[22] Filed: Oct. 7, 1976

[51] Int. Cl.² .................... C07D 213/55; C07C 63/26
[52] U.S. Cl. .......................... 260/295.5 R; 562/484; 562/490; 562/493
[58] Field of Search ......... 260/515 P, 515 R, 295.5 R

[56] References Cited

U.S. PATENT DOCUMENTS

| | | |
|---|---|---|
| 3,492,345 | 1/1970 | Neugebauer et al. ............ 260/515 P |
| 3,833,647 | 9/1974 | Gelbein et al. .................... 260/515 P |
| 3,920,670 | 11/1975 | Norton ........................... 260/295.5 R |
| 3,968,152 | 7/1976 | Sze et al. ........................... 260/515 P |

*Primary Examiner*—Alan L. Rotman
*Attorney, Agent, or Firm*—Marn & Jangarathis

[57] ABSTRACT

A nitrile, such as terephthalonitrile is catalytically reacted with water, in the vapor phase, to produce a gaseous effluent containing the corresponding carboxylic acid, as well as unreacted nitrile, ammonia and water. The acid product is separated from the gas by sublimation, preferably at a temperature above the dew point of the other components of the mixture.

17 Claims, 1 Drawing Figure

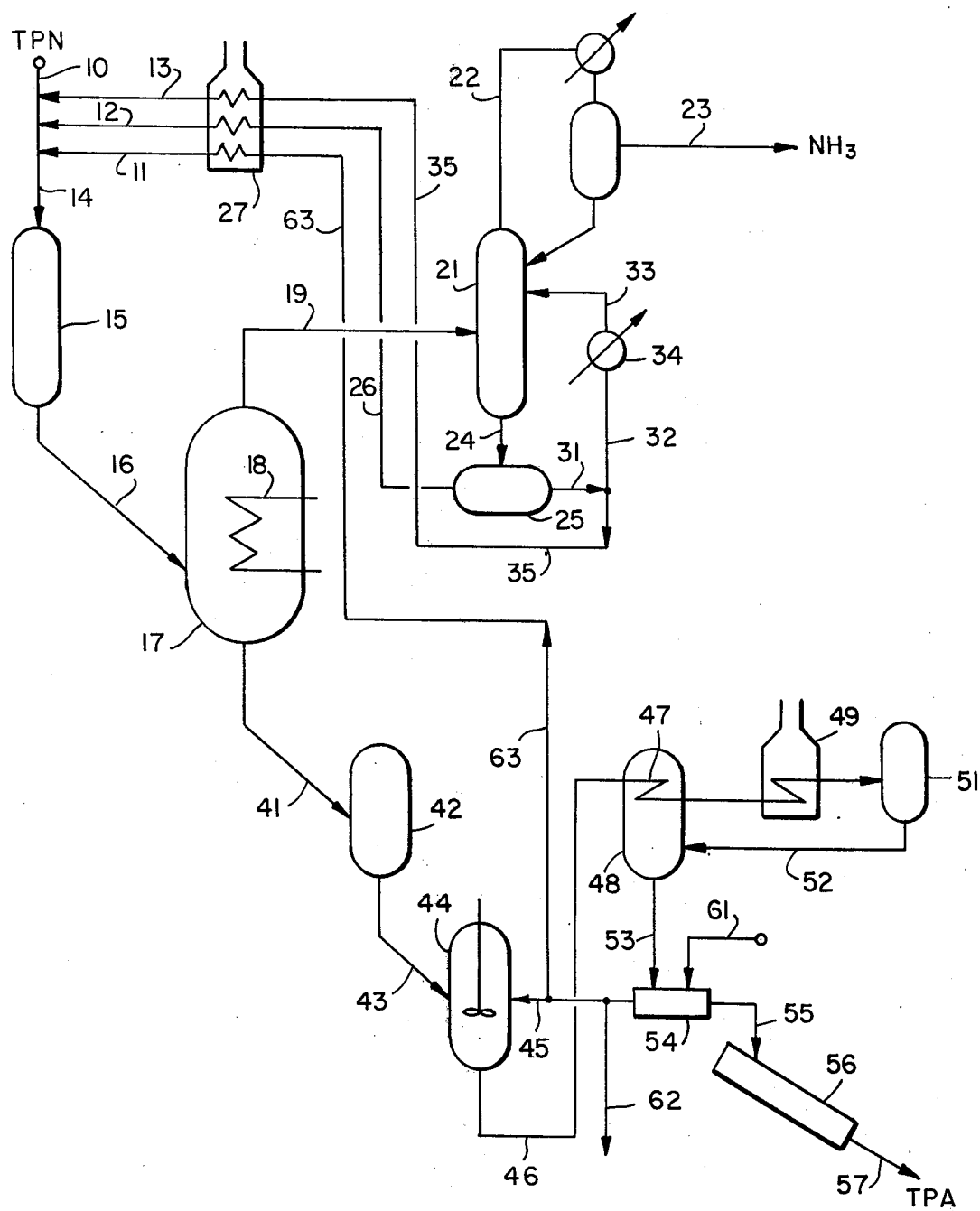

PRODUCTION OF CARBOXYLIC ACIDS FROM NITRILES

This invention relates to the production of carboxylic acids, and more particularly, to the production of carboxylic acids from nitriles.

Nitriles are generally converted to the corresponding carboxylic acid by aqueous hydrolysis which is catalyzed by an acid or base. Thus, for example, terephthalonitrile has been hydrolyzed with aqueous ammonia to produce the corresponding ammonium salt, which is then converted to the acid by steam stripping. Although such hydrolysis reactions are capable of producing the acid from the nitrile, there is a need for improvements in the production of carboxylic acids from nitriles.

An object of this invention is to produce a carboxylic acid.

A further object of this invention is to produce carboxylic acids from aromatic nitriles.

These and other objects of the present invention should be more apparent from reading the following detailed description thereof.

In accordance with the present invention, a nitrile and/or an intermediate hydrolysis product thereof is reacted with water, in the vapor phase, in the presence of a suitable catalyst to produce a gaseous effluent containing the corresponding acid and the acid is recovered from the gaseous effluent by sublimation.

The organic materials which are employed as starting materials for producing carboxylic acids in accordance with the present invention are either aromatic or heterocyclic nitriles. The aromatic nitriles contain one or more cyano-groups, preferably one or two cyano-groups and can be unsubstituted or substituted with other substituent groups; e.g., an alkyl group. the aromatic nucleus is preferably benzene or naphthalene. As representative examples, there may be mentioned: phthalonitrile, terephthalonitrile, isophthalonitrile, tolunitrile, 1-cyanonaphthalene, and 2,6-cyanonaphthalene. Similarly, the heterocyclic nitriles can contain one or more cyano groups, with the heterocyclic nucleus generally being pyridine. The preferred starting materials are nicotinonitrile, isophthalonitrile, terephthalonitrile and phthalonitrile. As hereinabove noted, the starting material may include a nitrile intermediate hydrolysis product, such as the imides, amides, cyano-acids, cyano-amides and amide-acids.

The catalyst employed for the vapor phase hydrolysis of the invention is a solid acid catalyst. As representative catalysts, there may be mentioned: silica gel, silica-alumina, supported phosphoric acid, Group III metal phosphates and sulfates, e.g., phosphates and sulfates of aluminum, boron and gallium, transition metal oxides; e.g., one or more oxides of vanadium, chromium, manganese, iron, cobalt, nickel, etc. The catalysts are of the type employed for hydration, dehydration and esterification reactions. The preferred catalyst is supported phosphoric acid.

The nitrile and water are reacted, in the vapor phase at temperatures which are generally of from 200° F to 1000° F, and preferably of from 400° F to 800° F. The temperatures which are employed are generally above the dew point of both the feed and product components. The temperatures are most preferably selected to provide at least a 50% conversion of the nitrile at a contact or reaction time of no greater than 1 minute.

The water is employed in at least stoichiometric proportions; however, an excess of water is preferably employed in that reaction kinetics are more favorable at higher water partial pressures. The stoichiometric excess of water can be as much as to provide a water to nitrile mole ratio of up to 500:1 with the water to nitrile mole ratio generally being from 5:1 to 50:1. The use of an excess of water also functions to maintain vapor phase conditions; however, an inert gaseous diluent, such as nitrogen, can be used for such purposes.

The total reaction pressure is generally selected to provide the desired water partial pressure, with such total pressures generally being from 1 to 10 atm.

The catalytic vapor phase reaction may be effected by any one of a wide variety of reaction techniques, including fixed bed, fluidized bed, dilute phase transport, etc., and the selection of a specific technique is deemed to be within the scope of those skilled in the art from the present teachings.

The gaseous effluent produced by the vapor phase reaction of nitrile and water contains the corresponding carboxylic acid, unreacted nitrile, unreacted water vapor, ammonia and reaction intermediates. The carboxylic acid is recovered from the effluent by sublimation of the carboxylic acid from the geseous effluent.

The temperature at which the sublimation of the acid from the effluent is effected varies with the particular carboxylic acid. As the temperature at which sublimation of the acid is effected decreases, there is an increase in the recovery of carboxylic acid from the vapor phase; however, as the temperature decreases below the dew point of the least volatile component, other than the acid product, in the reaction mixture, there is also an increase in the amount of other products sublimated from the vapor phase, which decreases the purity of the sublimated acid product. In general, the sublimation temperature is not less than 50° F below the dew point of the least volatile component; however, as should be apparent, it is preferred to effect sublimation of the acid at a temperature above the dew point of the least volatile component, other than the acid product, of the vapor effluent. The selection of a particular temperature to coordinate sublimated acid product purity with quantity of acid recovery is deemed to be within the scope of those skilled in the art from the persent teachings. In general, the temperature is selected to provide for at least 50% receovery of the acid product from the vapor phase.

The sublimation is preferably effected in the presence of solid carboxylic acid, with such solid carboxylic acid functioning both as a nucleus for crystal growth and a heat transfer agent for the sublimation.

The invention will be further described with respect to a specific embodiment thereof illustrated in the accompanying drawing wherein:

The drawing is a simplified schematic flow diagram of an embodiment of the present invention.

The embodiment will be specifically described with respect to the production of terephthalic acid; however, the embodiment is not limited to such production.

Referring to the drawing, vaporized terephthalonitrile in line 10 is combined with vaporized fresh feed water in line 11, vaporized recycle terephthalonitrile combined with a vaporized organic solvent therefor, such as xylene, in line 12, obtained as hereinafter described, and vaporized intermediate hydrolysis products, in line 13, obtained as hereinafter described, and the combined gas stream in line 14 is introduced into a terephthalic acid production reactor, schematically indicated as 15. Reactor 15, as hereinabove described, contains a suitable catalyst, such as phosphoric acid supported on silica-alumina, and in reactor 15 the water and terephthalonitrile react, in the gas phase, to produce terephthalic acid.

A gaseous reaction effluent, containing terephthalic acid, unreacted terephthalonitrile, unreacted water, ammonia, and reaction intermediate; in particular, terephthalamic acid and cyanobenzoic acid is withdrawn from reactor vessel 15 through line 16 and introduced into a terephthalic acid recovery vessel 17 wherein terephthalic acid is separated from the gaseous effluent by sublimation at a temperature above the dew point of the remaining components of the gaseous effluent. In this manner, terephthalic acid is recovered as a solid without condensation of the remaining components.

The recovery vessel 17 preferably includes solid terephthalic acid in a fluidized state to function as nucleation points for crystal growth and a heat transfer agent. The heat of desublimation is removed by the use of a cooling coil 18; however, it is to be understood that other heat exchange means, such as heat exchange jackets or direct water quench could also be employed.

In general, the recovery vessel is operated at a temperature of from 400° F to 600° F and at a pressure of from 1 to 3 atm. in order to effect recovery of the terephthalic acid by sublimation at above the dew point of the remaining components of the gaseous effluent.

A gaseous stream, containing water, ammonia, unreacted terephthalonitrile, p-xylene, cyanobenzoic acid, terephthalamic acid and a small amount of terephthalic acid, is withdrawn from recovery vessel 17 through line 19 and introduced into a quench vessel 21 to separate ammonia from the remaining components. In quench vessel 21 the gaseous stream is directly quenched by an aqueous quench liquid introduced through line 33 to condense a xylene solution of terephthalonitrile and an aqueous solution of the ammonium salts of terephthalic, cyanobenzoic and terephthalamic acid. By including a solvent for terephthalonitrile, such as p-xylene in the system the quench circuit is maintained free of solid terephthalonitrile. Similarly, by allowing the acids present in the gas stream to combine with ammonia and form water soluble ammonium salts the system is also maintained free of solids.

In general, the quench vessel 21 is operated at a temperature of from 100° F to 200° F and a pressure of from 1 to 3 atm.; however, it is to be understood that such conditions are merely illustrative.

A gaseous overhead is withdrawn from quench vessel 21 through line 22, which includes a suitable cooler and separator, and ammonia is withdrawn from the system through line 23.

Condensed liquid is withdrawn from quench vessel 21 through line 24 and introduced into a separator 25, with an organic phase of terephthalonitrile dissolved in p-xylene being withdrawn therefrom through line 26 and vaporized in heater 27 for recycle to reactor 15 through line 12.

An aqueous phase, containing the ammonium salts, is withdrawn from separator 25 through line 31, with a first portion thereof being passed through line 32, including a cooler 34 for use as quench liquid in line 33. The remaining portion of the aqueous phase is passed through line 35 and vaporized in heater 27 for introduction into reactor 15 through line 13.

Solid crude terephthalic acid, containing the partial hydrolysis product terephthalamic acid, is withdrawn from recovery vessel 17 through line 41 and introduced into a storage vessel 42 for ultimate purification.

As particularly shown, crude terephthalic acid withdrawn from storage vessel 42 through line 43 is repulped in vessel 44 in water introduced through line 45. A slurry of crude terephthalic acid in water is withdrawn from vessel 44 through line 46, heated in coil 47 positioned in the upper portion of flash crystallizer 48 and further heated in heater 49 to effect dissolution of the crude terephthalic acid. The solution of crude terephathalic acid is introduced into a hydrolysis vessel 51 wherein the solution is maintained at a temperature and a time sufficient to hydrolyze the terephthalamic acid to terephthalic acid. In general, the solution is maintained at a temperature of from 400° F to 600° F, with the time being in the order of from 30 minutes to 2 hours.

An aqueous solution of terephthalic acid is withdrawn from vessel 51 through line 52 and introduced into a flash crystallizer 48 to crystallize terephthalic acid. In general, the crystallizer 48 is operated at a temperature of from 100° F to 200° F and a pressure of from 1 to 5 atm. It is to be understood that such crystallization could be effected in one or more stages.

A slurry of terephthalic acid is withdrawn from crystallizer 48 through line 53 and introduced into a suitable separation vessel, such as centrifuge 54 to recover terephthalic acid.

A wet terephthalic acid cake is withdrawn from centrifuge 54 through line 55 and dried in drier 56, with the final pure terephthalic acid product being recovered through line 57.

A water wash is introduced into centrifuge 54 through line 62 and a first portion thereof employed in line 45 for repulping the crude terephthalic acid. A second portion is passed through line 63 and vaporized in heater 27 for introduction into the reactor 15 through line 11.

Although the invention has been described with respect to a specific embodiment, the scope of the invention is not to be limited thereby in that numerous modifications of the embodiment are possible within the overall scope of the invention. Thus, for example, the terephthalic acid product can be purified other than as particularly described.

In addition, the general embodiment may also be employed for the production of other acids; e.g., isophthalic acid.

The above modifications and others should be apparent to those skilled in the art from the present teachings.

The present invention is particularly advantageous in that it is possible to produce carboxylic acids of high purity, at lower pressures, in shorter times and with less expensive equipment. Thus, for example, the present invention can produce fiber grade terephthalic acid.

Numerous modifications and variations of the present invention are possible and, therefore, within the scope of the appended claims, the invention may be practiced otherwise than as particularly described.

What is claimed is:

1. In an acid catalyzed process for producing a carboxylic acid from a nitrile, the improvement comprising:
   reacting a nitrile selected from the group consisting of nicotinonitrile and aromatic nitriles wherein the aromatic nucleus is selected from the group consisting of benzene and naphthalene and water in the vapor phase in the presence of an acid catalyst in solid form to produce a gaseous effluent containing the corresponding carboxylic acid; and recovering the carboxylic acid from the gaseous effluent by sublimation of the carboxylic acid.

2. The process of claim 1 wherein the nitrile is an aromatic nitrile.

3. The process of claim 2 wherein the aromatic nitrile is benzene substituted with two cyano groups.

4. The process of claim 3 wherein the gaseous effluent includes ammonia, intermediate hydrolysis products and unreacted nitrile, with the unreacted nitrile and intermediate hydrolysis products being recovered and recycled to the reaction.

5. The process of claim 4 wherein the sublimation is effected at a temperature above the dew point of the least volatile component of the effluent other than the acid product.

6. The process of claim 5 wherein the gaseous effluent includes an organic solvent for the nitrile and subsequent to the sublimation the gaseous effluent is cooled to condense an aqueous solution of the intermediate hydrolysis products and a solution of the unreacted nitrile in the solvent, which are vaporized and recycled to the reaction.

7. The process of claim 6 wherein reaction of nitrile and water is effected at a temperature of from 200° F to 100° F.

8. The process of claim 7 wherein the catalyst is selected from the group consisting of silica gel, silica-alumina, supported phosphoric acid, Group III metal phosphates, Group III metal sulfates and transistion metal oxides.

9. The process of claim 8 wherein the catalyst is supported phosphoric acid.

10. The process of claim 8 wherein the nitrile is terephthalonitrile.

11. The process of claim 1 wherein the nitrile is nicotinonitrile.

12. In an acid catalyzed process for producing terephthalic acid from terephthalonitrile, the improvement comprising:

introducing water vapor, terephthalonitrile, an organic solvent for terephthalonitrile and recycle components, all in the vapor phase, into a terephthalic acid production zone, including an acid catalyst in solid form wherein the terephthalonitrile is hydrolized in the vapor phase to terephthalic acid;

withdrawing from the terephthalic acid production zone a gaseous reaction effluent containing terephthalic acid, terephthalonitrile, an organic solvent for terephthalonitrile, water vapor, ammonia and reaction intermediates;

introducing the gaseous effluent into a terephthalic acid recovery zone wherein terephthalic acid is separated from the gaseous effluent by sublimation at a temperature above the dew point of the remaining components of the gaseous effluent;

recovering solid terephthalic acid from the terephthalic acid recovery zone;

recovering remaining gaseous effluent from the terephthalic acid recovery zone;

quenching the remaining gaseous effluent to condense a solution of unreacted terephthalonitrile in the organic solvent for terephthalonitrile, and an aqueous solution of reaction intermediates;

and recovering and vaporizing terephthalonitrile solution and aqueous solution for recycle to the terephthalic acid production zone.

13. The process of claim 12 wherein a portion of the recovered aqueous solution is employed as a quench liquid for said quenching.

14. The process of claim 13 wherein said quenching is effected at a temperature of from 100° F to 200° F and a pressure of from 1-3 atmospheres.

15. The process of claim 12 wherein the hydrolysis is effected at a temperature of from 200° F to 1000° F.

16. The process of claim 15 wherein the catalyst is selected from the group consisting of silica gel, silica-alumina, supported phosphoric acid, Group III metal phosphates, Group III metal sulfates and transition metal oxides.

17. The process of claim 16 wherein the catalyst is supported phosphoric acid.

* * * * *